United States Patent [19]

Horii

[11] 4,279,728
[45] Jul. 21, 1981

[54] APPARATUS FOR DETERMINING ION CONCENTRATION

[75] Inventor: Yoshio Horii, Miyanohigashi, Japan

[73] Assignee: Horiba, Ltd., Kyoto, Japan

[21] Appl. No.: 144,932

[22] Filed: Apr. 29, 1980

[30] Foreign Application Priority Data

May 16, 1979 [JP] Japan .............................. 54-66737[U]

[51] Int. Cl.³ ...................... G01N 27/30; G01N 27/36
[52] U.S. Cl. ............................ 204/195 R; 204/195 G; 204/195 F
[58] Field of Search .......... 204/195 G, 195 F, 195 M, 204/195 R, 1 H; 324/438

[56] References Cited

U.S. PATENT DOCUMENTS

| | | | |
|---|---|---|---|
| 3,103,480 | 9/1963 | Watanabe et al. | 204/195 |
| 4,008,141 | 2/1977 | Kotani et al. | 204/195 G |
| 4,018,661 | 4/1977 | Brushwyler et al. | 204/195 F |
| 4,162,211 | 7/1979 | Jerrold-Jones | 204/195 G |

Primary Examiner—G. L. Kaplan

Attorney, Agent, or Firm—Wenderoth, Lind & Ponack

[57] ABSTRACT

An apparatus for determining the concentration of ions in a solution has an inner cylinder, and outer cylinder concentrically positioned around the inner cylinder and defining with the inner cylinder a chamber for holding an internal solution of a comparison electrode, and upper block and a lower block to which the upper and lower ends of the outer cylinder are sealingly connected, the blocks having holes therethrough and the ends of the inner cylinder being sealingly attached to the blocks in these holes. A comparison electrode tube is positioned in the chamber and has a liquid junction in the lower end and is open to the chamber adjacent the upper end, and an internal electrode of the comparison electrode is positioned within the comparison electrode tube. A measuring electrode is removably sealingly mounted in the hole in the lower block and extends downwardly from the lower blocks, and a further liquid junction is mounted in the lower block and extends from the chamber through the lower block.

6 Claims, 6 Drawing Figures

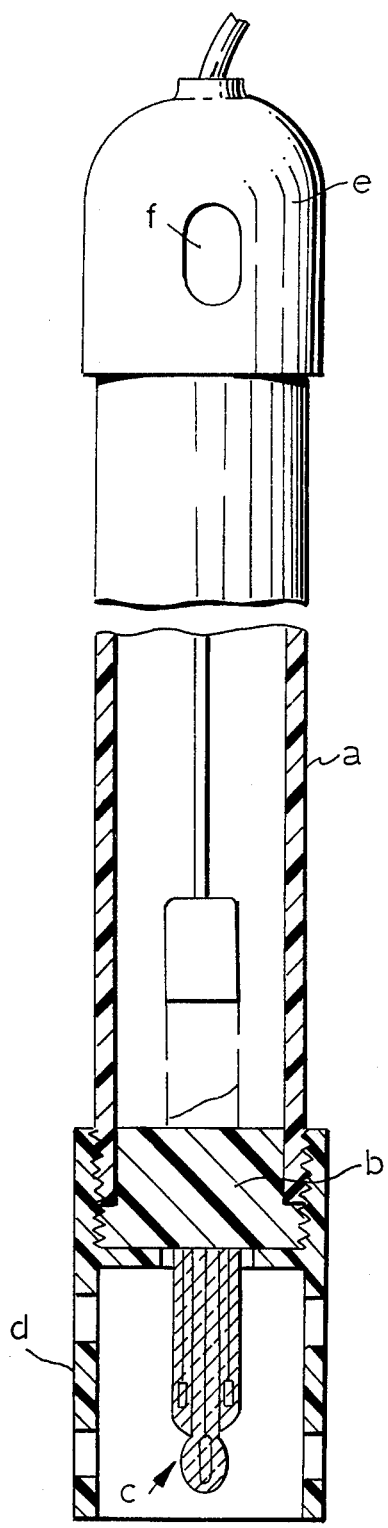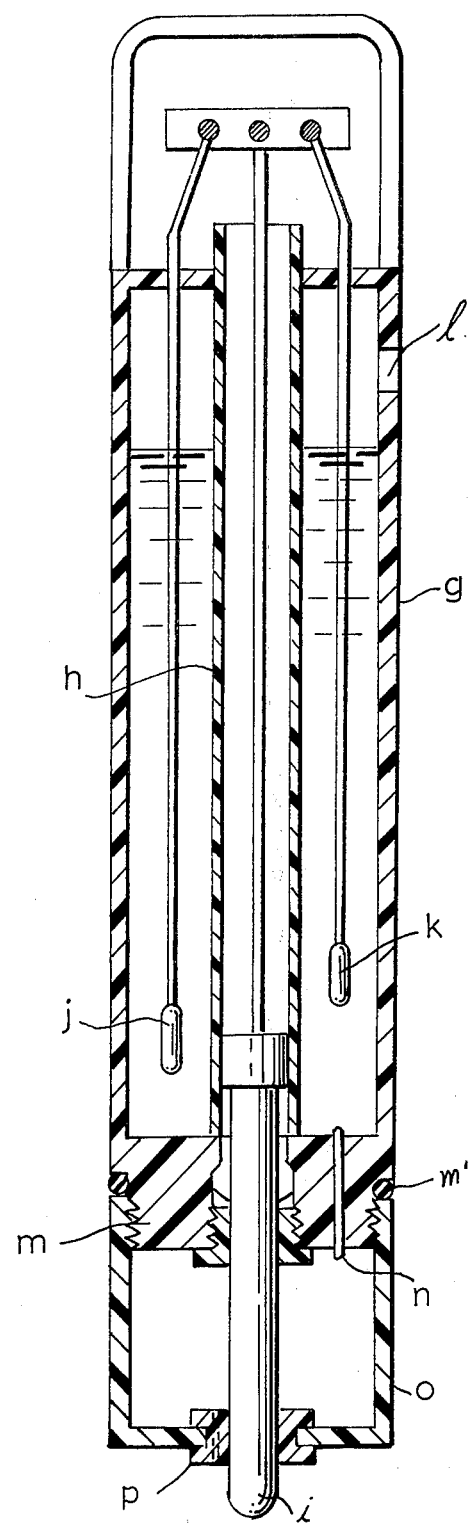
(PRIOR ART)
FIG.1
(PRIOR ART)
FIG.2

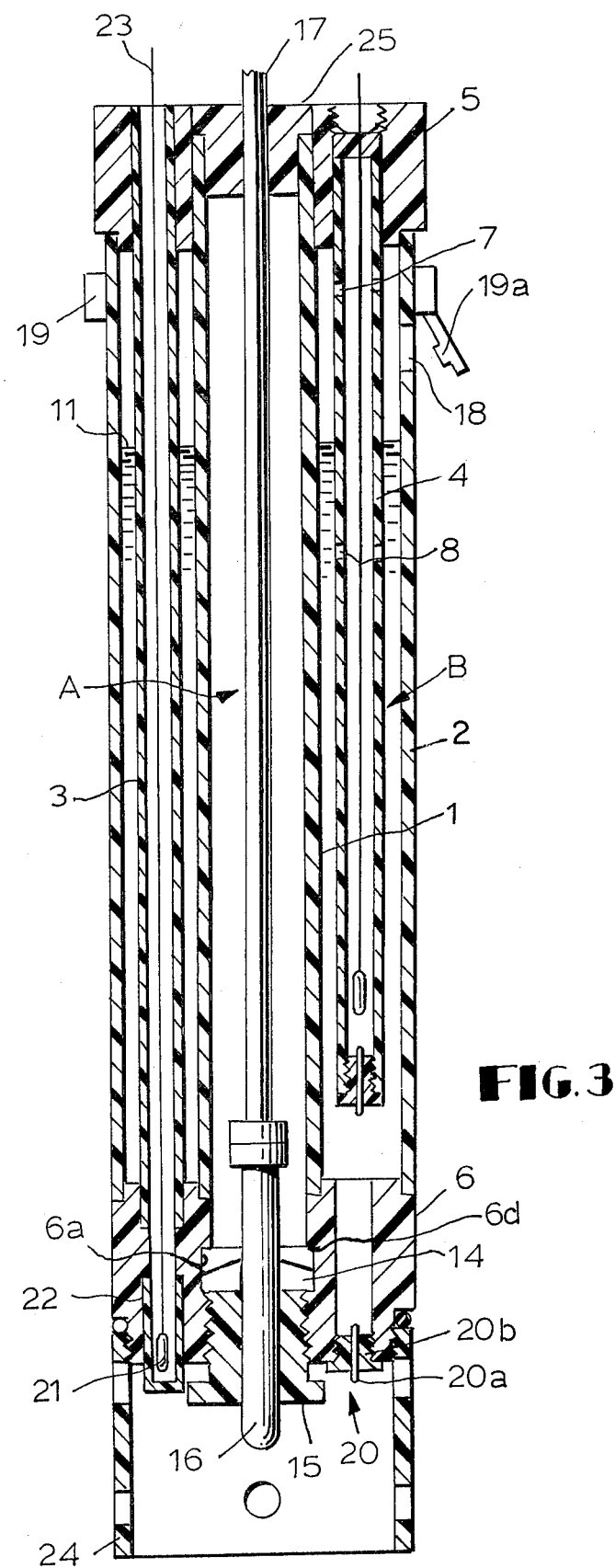
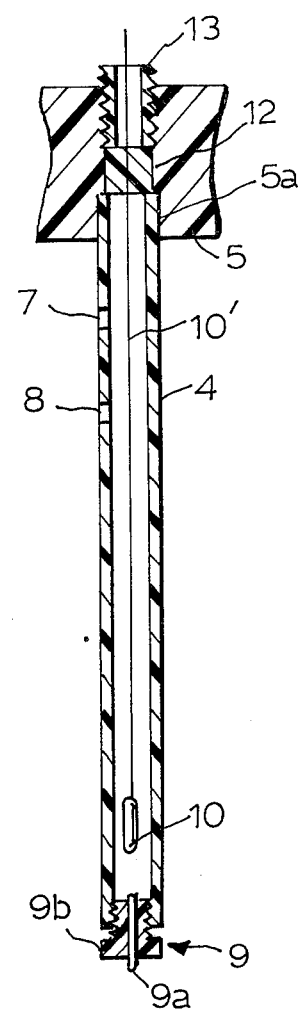
FIG.3
FIG.4

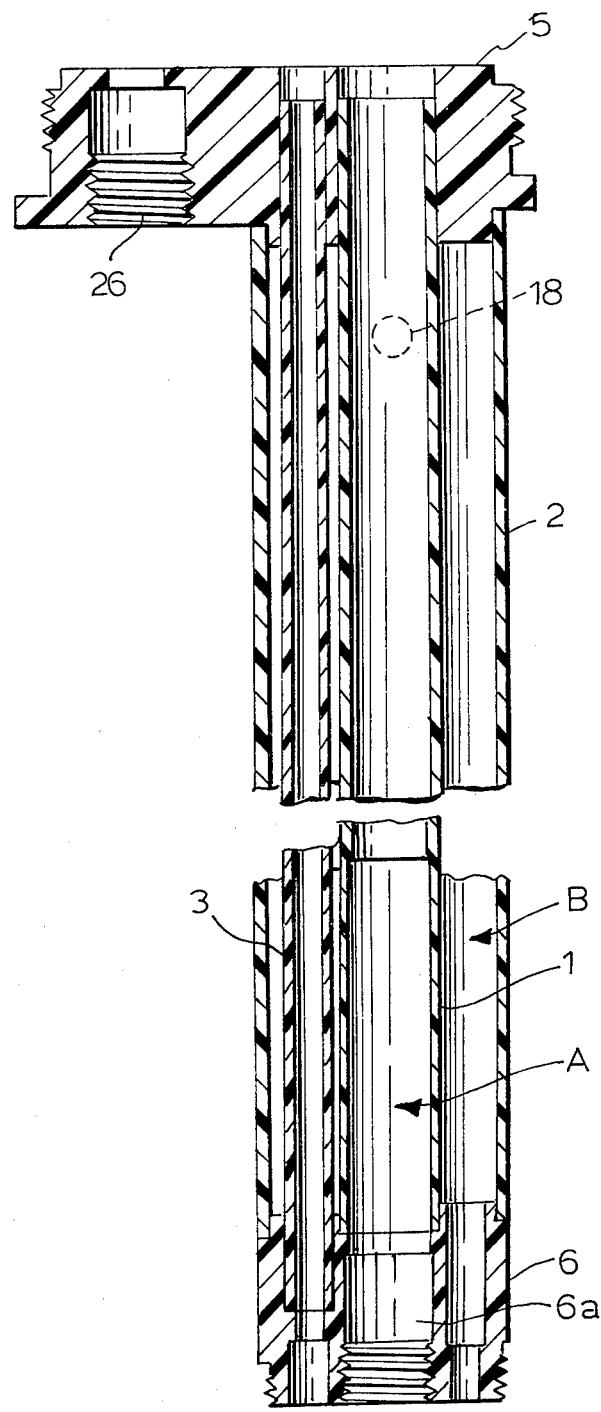
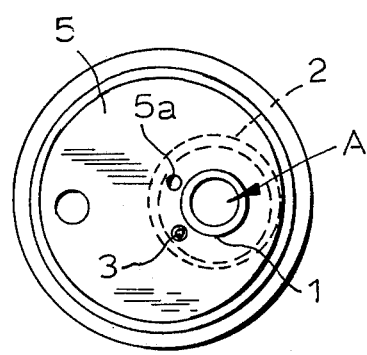
FIG.5
FIG.6

APPARATUS FOR DETERMINING ION CONCENTRATION

BACKGROUND OF THE INVENTION AND PRIOR ART

The present invention relates to an apparatus for determining concentration of ions in a solution.

Apparatus for determining concentration of ions which can operate for a long time by putting the internal solution of a comparison electrode into a cylindrical means for supporting electrodes, and having a construction as shown in FIG. 1 and FIG. 2 is well known.

FIG. 1 shows such an apparatus using a three-piece composite electrode of the single junction type and having a three-piece composite electrode (c) extending through an electrode packing (b) positioned in the lower portion of a hollow pipe (a) provided with an external thread and an electrode guard (d) threaded onto said pipe and surrounding the electrode (c). A KCl solution is introduced into the interior of the hollow pipe through an opening (f) formed in a protective cover (e) mounted on the end of said hollow pipe (a) at the other end from the packing (b). Although such a construction has the advantage that it is light and slim as a whole, it also has a defect that the insulation often breaks down because a pH electrode which requires a high insulation value such as $10^8 \Omega$ or more is immersed in a very permeable KCl solution. In addition, a back current or permeation of water to be tested may contaminate the comparison electrode and break down the internal electrode of the comparison electrode and thus give an abnormal indication in extreme cases when the pH electrode is immersed in water to be tested which has a high concentration of $Cl^-$ and $SO_3^-$. As to the maintenance, the exchanging of electrodes is difficult because all of the KCl solution contained in the means for supporting the electrodes must be drained or discarded, and moreover the entire electrode (c) must be exchanged when a glass electrode has been broken even though the comparison electrode does not have any abnormalities. This is very uneconomical.

FIG. 2 shows a prior art apparatus using a supporter of the double-junction type which can also be used as a comparison electrode and which has a double cylinder consisting of a closed hollow cylinder (g) and a further hollow pipe (h) extending coaxially therethrough, the internal pipe (h) having a glass electrode (i) fixedly mounted therein, an internal electrode (j) of the comparison electrode and an element (k) for determining temperature being positioned in the space between said external cylinder (g), and KCl solution being introduced into said space through an opening (l) in the upper portion of said external cylinder (g). In addition, a block (m) is provided at the lower end of cylinder (g) for fixing the glass electrode on the lower portion of said external cylinder (g) and has a liquid junction (n) extending therethrough, said block (m) having a cylinder (o) threaded thereon with a packing (m') between it and said cylinder (g), said cylinder (o) further having a packing (p) which also serves as a liquid junction at the lower portion thereof, the tip portion of the glass electrode (i) extending through said packing (p).

Although such a construction provides very effective insulation because said glass electrode (i) itself extends from a space separate from KCl solution, said glass electrode cannot be exchanged until the lowermost junction formed by the packing (p) is removed, and KCl solution contained in said cylinder (o) must be transferred to another vessel or discarded. Also, it is necessary that the caliber of said junction (n) be comparatively large because KCl solution must be transferred through the junction (n) from the space between said internal cylinder (h) and said external cylinder (g) to said lower cylinder (o) through said junction (n). Therefore, in practice, the advantage of the double-junction is greatly restricted. It takes a long time to transfer KCl solution from the space within cylinder (g) to the cylinder (o) if said junction (n) is made of ceramic or the like in order to increase the double-junction effect. Even though such a difficult problem of the junction could be solved, this construction nevertheless causes KCl solution to flow out of the system, and there is thus the possibility that the KCl solution in tube (g) will be lost even though KCl solution will remain in said cylinder (o). Under such a condition, it is impossible to determine the concentration of ions because the internal electrode (j) is no longer immersed.

OBJECT AND BRIEF SUMMARY OF THE INVENTION

The apparatus for determining the concentration of ions according to the present invention was developed taking into account the above-mentioned defects. The object of the present invention is to provide an apparatus for determining the concentration of ions which is easy to maintain and which can reduce the running cost, and yet which will make a stable determination of the ion concentration over a long period of time. Such an object is attained by providing a double cylinder consisting of an internal cylinder and an external cylinder with the upper end portion and the lower end portion of said double cylinder held in blocks for defining an internal space within said internal cylinder as an inner chamber for enclosing a measurement electrode fixed in a hole in the lower block so as to be able to be freely inserted or pulled out, and for defining a space between said internal cylinder and said external cylinder as an outer chamber for enclosing an internal solution of a comparison electrode, said lower block also being provided with a junction. The outer chamber has therein a tube for enclosing an internal electrode of the comparison electrode, which tube depends from the upper block, said tube having a small hole at the upper end communicating with said outer chamber and a junction at the lower end portion. An internal electrode of the comparison electrode as well as the internal solution are contained inside said tube.

The following effects are achieved by this construction:

a. The comparison electrode is protected from the solution to be tested which may contain a large amount of $Cl^-$ and $SO_3^-$ ions, because the double-junction construction is provided, i.e. a junction in said lower block and are in the lower end portion of the tube enclosing the internal electrode of the comparison electrode. Accordingly, a stable measure is possible.

b. A stable measurement over a long period of time is possible because bubbles do not contact the surface of the internal electrode of the comparison electrode even though they are generated when the internal solution contained in the chamber B flows out. Moreover, the internal electrode of the comparison electrode is never uncovered by the solution when some of the solution in the chamber flows out through the junction in the lower block, even though the level of the solution may vary to some extent depending on the space between the upper surface of said lower block and the lower end of the tube for enclosing the internal electrode of the comparison electrode as well as the space between the lower end of the tube for enclosing the internal electrode of the comparison electrode and the internal electrode within said tube, and consequently the solution is used economically.

c. Difficulties such as bad insulation can be easily avoided even though the measurement electrode, such as a glass electrode, for determining pH and which requires good insulation is used, because the measurement electrode is positioned in a space separated from the internal solution. d. A stable operation for a long time, easy maintenance and a decrease of the operating cost are made possible because the maintenance requires only an exchange of the measurement electrode which is expendable.

e. The internal solution will not be lost from the system when the measurement electrode is detached for being replaced even though the apparatus has a double-junction, because the second junction of the double-junction is separate from the supporting structure for the measuring electrode and is not removed when replacing the measuring electrode, and consequently it is not necessary to collect the solution in another vessel or discard it when exchanging the measurement electrode.

BRIEF DESCRIPTION OF THE DRAWINGS

FIG. 1 and FIG. 2 are longitudinal sectional views showing examples of prior art apparatus for measuring ion concentration;

FIG. 3 is a longitudinal sectional view of the apparatus of the present invention;

FIG. 4 is a longitudinal sectional view of one of the main parts thereof;

FIG. 5 is a partially cut off longitudinal sectional view showing constituent elements thereof; and FIG. 6 is a plan view of the elements of FIG. 5.

DESCRIPTION OF THE PREFERRED EMBODIMENTS

FIG. 3 to FIG. 6 show examples of an apparatus for determining the concentration of ions according to the present invention. The apparatus consists of a central cylinder 1 constituted by a pipe preferably of plastic, an outer cylinder 2 concentrically positioned around the central pipe 1 and constituted by a pipe also preferably of plastic, a tube 3 for enclosing an element for sensing temperature and a tube 4 for enclosing an internal electrode of a comparison electrode, the tubes being small pipes also preferably of plastic and positioned in the annular space B between the central and outer cylinders. The outer cylinder 2 has the upper end engaged in the upper block 5 and the lower end engaged in the lower block 6 and the ends are fixed in the blocks by means of adhesive, welding or the like. Both the upper end and the lower end of said central cylinder 1 are inserted into the holes formed in the central portion of said upper block 5 and said lower block 6 and both the upper end and the lower end of said tube 3 for enclosing the temperature sensing element are inserted into small diameter holes formed in said upper block 5 and said lower block 6, and the ends of the respective cylinder and tube are fixed in the holes by means of adhesive, welding or the like.

As shown in FIG. 4, the tube 4 for enclosing an internal electrode of a comparison electrode is provided near the upper end with a small hole 7 of suitable diameter (for example, 2 to 3 mm in diameter) which functions as an air vent and a small hole 8 just below the hole 7 for introducing the solution into the tube 4. A rubber packing 9b is positioned in the lower open end of said small tube 4 and it holds a porous ceramic rod 9a or the like which acts as a liquid junction 9, ie. . a means for bringing fluids at opposite ends thereof into contact. An internal electrode 10 of a comparison electrode, a lead wire 10' coated with paint or surrounded by a tube to protect the wire from contact with a solution in the tube 4 are positioned within said tube 4 and the upper end portion of said tube 4 is inserted into a small hole 5a formed in said upper block 5 and mounted so as to be suspended in the space B by adhesive, welding or the like. The lead wire 10' extends through a packing 12 and a threaded coupling 13 in the upper block 5.

The space A within said central cylinder 1 is a chamber for enclosing a conventional measurement electrode 16, such as a glass electrode, for determining pH, and the upper portion of the measurement electrode 16 is held in a hole 6a at the central portion of said lower block 6 by a packing 14 in liquid tight engagement around the electrode and urged against a seat 6d in the hole 6a by an apertured threaded plug 15 threaded into the hole 6a, whereby the electrode 16 can be freely inserted into or removed from the hole 6a. An electrode cable 17 extends from said mesurement electrode 16 through the upper block 5.

The space B between said central cylinder 1 and said outer cylinder 2 forms a chamber enclosing an internal solution 11 of the comparison electrode in which said internal electrode 10 must be immersed. An inlet 18 is provided at the upper end of the outer cylinder 2 for introducing said solution 11 into the space B. A band 19 is positioned around the upper end of tube 2 and has a projecting portion 19a hinged thereon for closing said inlet 18. A liquid junction 20 is provided in said lower block 6, and is constituted by a porous ceramic rod 20a held in a rubber packing 20b which is threaded into the lower end of a bore 6d. Other types of junctions can be used, such as a pin hole, a sleeve having a glass tube therein, a fiber junction or the like.

A stopper-like element 22 is inserted in the hole in lower block 6 in which the end of tube 3 is inserted, and element 22 is fixed by means of adhesive, welding or the like. A temperature sensing element 21 is suspended within element 22 on a cable 23 which extends through tube 3 and through said upper block 5. A guard 24 is threaded onto the lower end of said lower block 6. A rubber packing 25 is provided in the upper block 5 so that it can be freely inserted or removed. Furthermore, as shown in FIG. 5 and FIG. 6, said upper block 5 can have a diameter two to three times that of said outer cylinder 2, said central cylinder 1 and said external cylinder 2 being positioned eccentrically in said upper block 5, and a wiring port 26 can be provided in one side of said upper block 5 to permit pulling a cable from the underside of said block, and there can be a means for amplifying the detected pH or the like (not shown) on said upper block 5.

Pipes or tubes having a cross-sectional shape other than circular, such as square pipes, can be used for cylinders 1 and 2 and tubes 3 and 4 instead of pipes having a circular cross-sectional shape. In the preferred embodiment, the tube 3 for enclosing the temperature sensing element and the tube 4 for enclosing the internal electrode of the comparison electrode are pipes with an internal diameter of 4 mm and an outer diameter of 6 mm, the internal cylinder 1 is a pipe with an inside diameter of 16 to 18 mm and an outer diameter of 22 mm, and the outer cylinder 2 is a pipe with an inside diameter of 48 mm. However, other size pipes may be used depending on the circumstances. The upper block 5 and the lower block 6 must be sufficiently large to accommodate the supplementary elements, for example the guard 24, the junction 20, the packings 12 and 14, the plugs 13 and 15 and the like. In a practical embodiment the upper block 5 has a diameter of 60 to 150 mm and a thickness of 20 mm or more and the lower block 6 has a diameter of 48 mm or more and a thickness of 35 mm or more.

In the use of the apparatus for measuring the concentration of ions, the measurement electrode 16 is mounted in the bottom block 6 by means of the packing 14 and the plug 15 and the electrode cable 17 is pulled through the upper block 5, and then the predetermined quantity (500 to 750 ml in the present embodiment) of the internal solution (KCl solution is used in the present preferred embodiment) is introduced through the inlet port 18 in the external cylinder 2, and then the guard 24 is mounted on the lower block 6. The thus prepared apparatus has the lower end with measuring electrode thereon dipped in the solution to be tested.

What is claimed is:

1. An apparatus for determining the concentration of ions in a solution, comprising:
    an inner cylinder;
    an outer cylinder concentrically positioned around said inner cylinder and defining with said inner cylinder a chamber for holding an internal solution of a comparison electrode;
    an upper block and a lower block to which the upper and lower ends of said outer cylinder are sealingly connected, said blocks having holes therethrough and the ends of said inner cylinder being sealingly attached to said blocks in said holes;
    a comparison electrode tube depending from said upper block into said chamber and having a liquid junction in the lower end of said tube, said tube being open to said chamber adjacent the upper end thereof;
    an internal electrode of the comparison electrode positioned within said comparison electrode tube and having a lead extending out of the upper end of said tube through said upper block;
    a measuring electrode removably sealingly mounted in said hole in said lower block and extending downwardly from said lower block; and
    a further liquid junction mounted in said lower block and extending from said chamber through said lower block.

2. An apparatus as claimed in claim 1 in which said comparison electrode tube is a circular cross-sectional tube.

3. An apparatus as claimed in claim 1 in which said comparison electrode tube is mounted in said upper block for being freely removable and insertable through said upper block.

4. An apparatus as claimed in claim 1 in which said hole in said lower block has a seat therein, and means is provided for mounting said measuring electrode in said hole and comprising a packing around said measuring electrode in sealing engagement therewith and seated against said seat, and an apertured plug around said measuring electrode and threaded into said hole and urging said packing against said seat.

5. An apparatus as claimed in claim 1 further comprising a temperature sensing element tube connected between said upper and lower blocks and extending through said chamber, said lower block having a bore therethrough and a stopper in the lower end of said bore, and a temperature sensing element positioned in said bore and having a lead extending through said temperature sensing element tube and through said upper block.

6. An apparatus as claimed in claim 1 further comprising a cylindrical guard detachably mounted on the lower end of said lower block and surrounding the lower end of said measuring electrode.

* * * * *